United States Patent
An

(10) Patent No.: US 11,207,148 B2
(45) Date of Patent: Dec. 28, 2021

(54) DEVICES, SYSTEMS, AND METHODS ENABLING UTILIZATION OF SURGICAL PACKAGING AS A SURGICAL DRAPE

(71) Applicant: COVIDIEN LP, Mansfield, MA (US)

(72) Inventor: Allen X. An, Woburn, MA (US)

(73) Assignee: Covidien LP, Mansfield, MA (US)

( * ) Notice: Subject to any disclaimer, the term of this patent is extended or adjusted under 35 U.S.C. 154(b) by 493 days.

(21) Appl. No.: 16/140,778

(22) Filed: Sep. 25, 2018

(65) Prior Publication Data

US 2020/0093557 A1    Mar. 26, 2020

(51) Int. Cl.
  *A61B 46/10* (2016.01)
  *A61B 46/23* (2016.01)
  *A61B 50/30* (2016.01)
  *A61B 46/20* (2016.01)
  *A61B 50/00* (2016.01)

(52) U.S. Cl.
  CPC .............. *A61B 46/23* (2016.02); *A61B 46/10* (2016.02); *A61B 50/30* (2016.02); *A61B 2046/205* (2016.02); *A61B 2046/236* (2016.02); *A61B 2050/0065* (2016.02)

(58) Field of Classification Search
  CPC ......... A61B 50/30; A61B 50/36; A61B 50/37; A61B 2050/0065; A61B 2050/375; A61B 46/23; A61B 46/10; A61B 2046/205; A61B 2046/236

USPC ........................................ 206/438, 363, 370
See application file for complete search history.

(56) References Cited

U.S. PATENT DOCUMENTS

| | | | | |
|---|---|---|---|---|
| 4,928,830 A | * | 5/1990 | Brewer ................. | A61B 50/31 206/363 |
| 5,709,221 A | * | 1/1998 | Vancaillie ............... | A61B 1/12 128/849 |
| 6,179,819 B1 | * | 1/2001 | Haswell .............. | A61M 1/0236 128/854 |
| 6,436,085 B1 | * | 8/2002 | Lauer .................... | A61M 39/10 604/408 |
| 8,417,030 B2 | * | 4/2013 | Peng ...................... | G06T 5/003 382/167 |

\* cited by examiner

*Primary Examiner* — Steven A. Reynolds
(74) *Attorney, Agent, or Firm* — Carter, DeLuca & Farrell LLP

(57) ABSTRACT

Devices, systems, and methods facilitating surgery include surgical packaging transitionable from a furled configuration to an unfurled configuration. In the furled configuration, the surgical packaging is configured to enclose at least one surgical component therein. In the unfurled configuration, the at least one surgical component is removed from the surgical packaging and the surgical packaging is configured for use during a surgical procedure.

10 Claims, 2 Drawing Sheets

DEVICES, SYSTEMS, AND METHODS ENABLING UTILIZATION OF SURGICAL PACKAGING AS A SURGICAL DRAPE

BACKGROUND

1. Technical Field

The present disclosure relates generally to surgical procedures and, more particularly, to devices, systems, and methods enabling the use of surgical packaging as a surgical drape.

2. Background of Related Art

Surgical components such as devices, instruments, accessories, adapters, tube sets, etc., are typically enclosed in surgical packaging during final stages of manufacturing or reprocessing in order to maintain the sterility of the components. The surgical packaging itself may also be sterile. Surgical components may be packaged in surgical packaging individually, or may be packaged in surgical kits including multiple components used with one another and/or during the same surgical procedure(s). Typically, the surgical packaging is discarded once the packaging is opened and the surgical component(s) removed.

Surgical procedures, such as tissue resection procedures, may utilize one or more surgical kits packaged in surgical packaging and/or one or more surgical components individually packaged in surgical packaging. Tissue resection procedures may be performed endoscopically within an organ, such as a uterus, by inserting a hysteroscope into the uterus and passing a tissue resection device through the hysteroscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space. A surgical drape is often placed underneath the patient during intrauterine tissue resection procedures to collect any leaked fluid. Additional or alternative surgical drapes may be utilized to form a sterile barrier in intrauterine tissue resection procedures.

SUMMARY

To the extent consistent, any or all of the aspects described herein may be used in conjunction with any or all of the other aspects described herein.

Provided in accordance with aspects of the present disclosure is a device facilitating surgery. The device includes surgical packaging including at least one base layer and at least one cover layer. The surgical packaging is transitionable from a furled configuration to an unfurled configuration. In the furled configuration, the at least one base layer and the at least one cover layer are connected to one another along at least a portion of a perimeter of the surgical packaging such that the surgical packaging is configured to enclose at least one surgical component therein. In the unfurled configuration, at least a portion of the connection between the at least one base layer and the at least one cover layer is broken to at least partially separate the at least one base layer from the at least one cover layer such that the surgical packaging is configured for use during a surgical procedure.

In an aspect of the present disclosure, in the unfurled configuration, the surgical packaging defines a funnel-shaped configuration including a body, a mouth defined at one end of the body, and an opening defined at an opposite end of the body.

In another aspect of the present disclosure, the surgical packaging further includes a drape line attached to at least one of the at least one base layer or the at least one cover layer. The drape line is connected to or connectable to the opening in the unfurled configuration of the surgical packaging.

In yet another aspect of the present disclosure, in the unfurled configuration, the surgical packaging defines an exposed surface area greater than an exposed surface area of the surgical packaging in the furled configuration. The surgical packaging may define an exposed surface area at least two times greater than the exposed surface area of the surgical packaging in the furled configuration.

A system facilitating surgery provided in accordance with aspects of the present disclosure includes at least one surgical component and surgical packaging including at least one base layer and at least one cover layer. The surgical packaging is transitionable from a furled configuration to an unfurled configuration. In the furled configuration, the at least one base layer and the at least one cover layer are connected to one another along at least a portion of a perimeter of the surgical packaging to enclose the at least one surgical component therein. In the unfurled configuration, at least a portion of the connection between the at least one base layer and the at least one cover layer is broken to at least partially separate the at least one base layer from the at least one cover layer such that the at least one surgical component may be removed from the surgical packaging and such that the surgical packaging is configured for use during a surgical procedure.

In an aspect of the present disclosure, in the unfurled configuration, the surgical packaging defines a funnel-shaped configuration including a body and a mouth defined at one end of the body.

In another aspect of the present disclosure, the at least one surgical component is configured for use during a tissue resection procedure and the surgical packaging is configured to collect leaked fluid during the tissue resection procedure.

In yet another aspect of the present disclosure, the funnel-shaped configuration further defines an opening at an opposite end of the body. In such aspects, the surgical packaging may further include a drape line attached to at least one of the at least one base layer or the at least one cover layer, the drape line connected to or connectable to the opening in the unfurled configuration of the surgical packaging.

In still another aspect of the present disclosure, in the unfurled configuration, the surgical packaging defines an exposed surface area greater than an exposed surface area of the surgical packaging in the furled configuration. The exposed surface area in the unfurled configuration may be at least two times greater than the exposed surface area in the furled configuration.

In still yet another aspect of the present disclosure, the at least one surgical component includes a plurality of single-patient-use components.

A method facilitating surgery provided in accordance with aspects of the present disclosure includes obtaining surgical packaging enclosing at least one surgical component therein, removing the at least one surgical component from the surgical packaging, and utilizing the surgical packaging during a surgical procedure.

In an aspect of the present disclosure, using the surgical packaging during the surgical procedure includes collecting fluid with the surgical packaging.

In another aspect of the present disclosure, the surgical packaging is obtained in a furled configuration and removing the at least one surgical component includes at least partially unfurling the surgical packaging.

In still another aspect of the present disclosure, the surgical packaging is obtained in a furled configuration and the method further includes, prior to utilizing the surgical packaging, unfurling the surgical packaging to an unfurled configuration.

In yet another aspect of the present disclosure, unfurling the surgical packaging includes at least partially separating at least one base layer of the surgical packaging from at least one cover layer of the surgical packaging.

In still yet another aspect of the present disclosure, in the unfurled configuration, the surgical packaging defines an exposed surface area greater than an exposed surface area of the surgical packaging in the furled configuration.

In another aspect of the present disclosure, the method further includes utilizing the at least one surgical component during the surgical procedure.

In another aspect of the present disclosure, the method further includes discarding the at least one surgical component and the surgical packaging after the surgical procedure.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

The present disclosure provides devices, systems, and methods that enable the use of surgical packaging as a surgical drape, thereby reducing material waste. More specifically, the present disclosure provides surgical packaging that is initially utilized to maintain the sterility of surgical component(s) enclosed therein and that is subsequently utilized, after removal of the surgical component(s), as a surgical drape to, for example, collect fluids, maintain a sterile barrier, serve as a divider, etc. Although detailed herein with respect to a surgical kit facilitating an intrauterine tissue resection procedures, the devices, systems, and methods of the present disclosure are equally applicable for use in other surgical procedures and/or with other surgical components.

Figure 1:
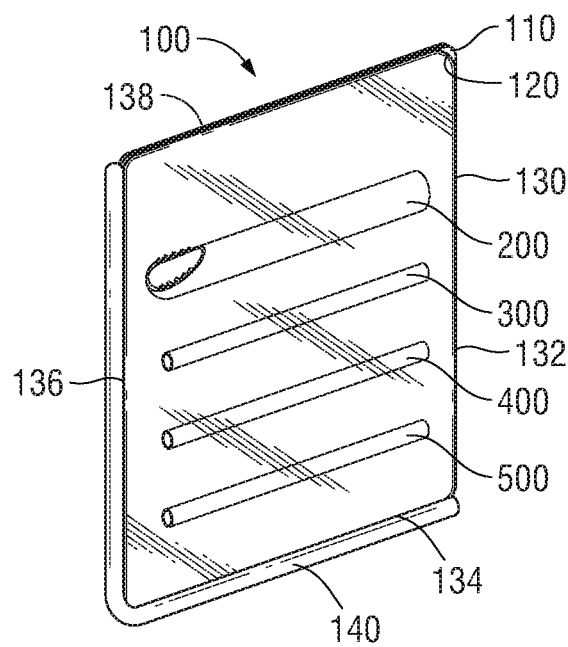
FIG. 1 is a perspective view of surgical packaging in a furled configuration enclosing surgical components therein.

Turning to FIG. 1, surgical packaging 100 is illustrated enclosing one or more surgical components 200, 300, 400, 500 to maintain the sterility of the surgical component(s) 200-500. Surgical packaging 100 may itself be sterile. Surgical components 200-500 may include, for example, one or more (similar or different) tissue resecting end effector assemblies 200 as well as surgical tubing 300, 400, 500 of similar or different configurations. However, additional or alternative surgical components are also contemplated. Surgical components 200-500 may be single-patient-use components and surgical packaging 100 may be configured to include the necessary single-patient-use components to enable one surgical packaging 100 to be utilized for a particular surgical procedure and/or surgical task (alone or in combination with re-usable components). Alternatively, surgical components 200-500 may be re-usable components capable of being sterilized or reprocessed for further use, or may include both single-patient-use and re-usable components.

As noted above, surgical packaging 100 may include single-patient-use components 200-500 that, together with other re-usable components (not shown) and/or single-patient-use components (not shown), enable one surgical packaging 100 to be utilized for a particular surgical procedure and/or surgical task. For example, with respect to an intrauterine tissue resection procedure, components 200-500 of surgical packaging 100 may be utilized with re-usable components such as a surgical handpiece connected to a control box, a hysteroscope, a fluid management system, and a fluid collection system. More specifically, tissue resecting end effector assembly 200 may be engagable with the surgical handpiece for use therewith, and tubing 300, 400, 500 may be connected between two or more of the tissue resecting end effector assembly 200, surgical handpiece, hysteroscope, fluid management system, and fluid collection system to enable the inflow and outflow of fluid during the intrauterine tissue resection procedure. Exemplary configurations of tissue resecting end effector assemblies, re-usable surgical handpieces, control boxes, hysteroscopes, fluid management systems, and/or fluid collection systems, as well as use of the same in an intrauterine tissue resection procedure, are described in one or more of U.S. Pat. No. 8,062,214 entitled "Tissue Resecting System," U.S. Patent Application Pub. No. 2018/0146979 entitled "Surgical Instrument with Suction Control," and/or U.S. Pat. No. 10,004,385 entitled "Oblique Tip Endoscope with Zero Degree Field Angle," the entire contents of each of which is hereby incorporated herein by reference.

Continuing with reference to FIG. 1, surgical packaging 100 is initially disposed in a furled configuration storing surgical components 200-500 therein. In the furled configuration, surgical packaging 100 is folded to define a generally rectangular-shaped configuration (or other suitable configuration) including a plurality of layers of material having at least one base layer 110 and at least one cover layer 120. Surgical components 200-500 are disposed between the base layer(s) 110 and the cover layer(s) 120 with, in the unfurled configuration, the base layer(s) 110 and the cover layer(s) 120 formed with one another, joined to one another, sealed with one another, and/or otherwise connected to one another (directly or indirectly) along at least a portion of outer perimeter 130, e.g., first, second, third and/or fourth sides 132, 134, 136, 138, respectively, of surgical packaging 100 to retain surgical components 200-500 therein and maintain the sterility of surgical components 200-500 within surgical packaging 100. Adhesives, mechanical engagements, e.g., hook and loop fasteners, heat-sealing, etc., may be utilized to connect the base layer(s) 110 and the cover layer(s) 120 along the at least a portion of outer perimeter 130. Further, the cover layer(s) 120 and/or the base layer(s) 110 may be transparent or partially-transparent to enable a user to view the surgical components 200-500 within surgical packaging 100 without the need to open surgical packaging 100.

Referring still to FIG. 1, in embodiments, a drape line 140 extends along one or more of the sides 132-138 of surgical packaging 100 in the furled configuration thereof. In the furled configuration, drape line 140 may serve to connect the base layer(s) 110 and the cover layer(s) 120 with one another along one or more sides 132-138 of outer perimeter 130 of surgical packaging 100, or may simply be attached to surgical packaging 100 along the one or more sides 132-138 of outer perimeter 130 in any suitable manner, e.g., via adhesives, mechanical engagements, heat-sealing, etc.

Figure 2:
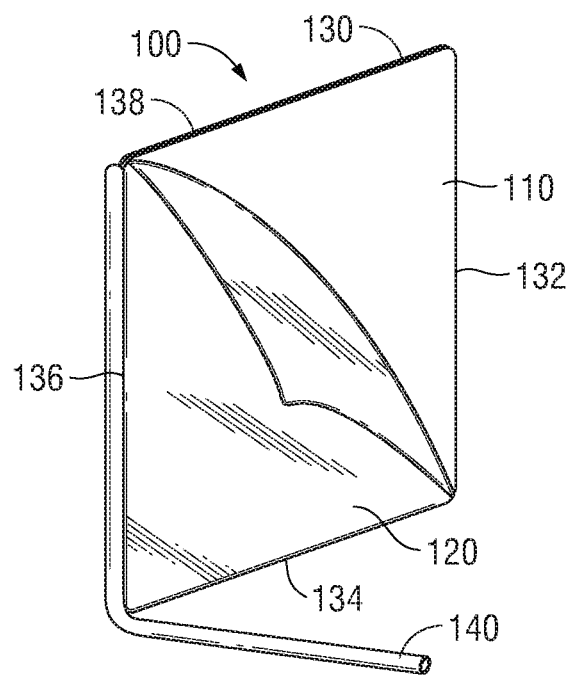
FIG. 2 is a perspective view of the surgical packaging of FIG. 1 with the surgical components removed and the surgical packaging in a partially unfurled configuration.
Figure 3:
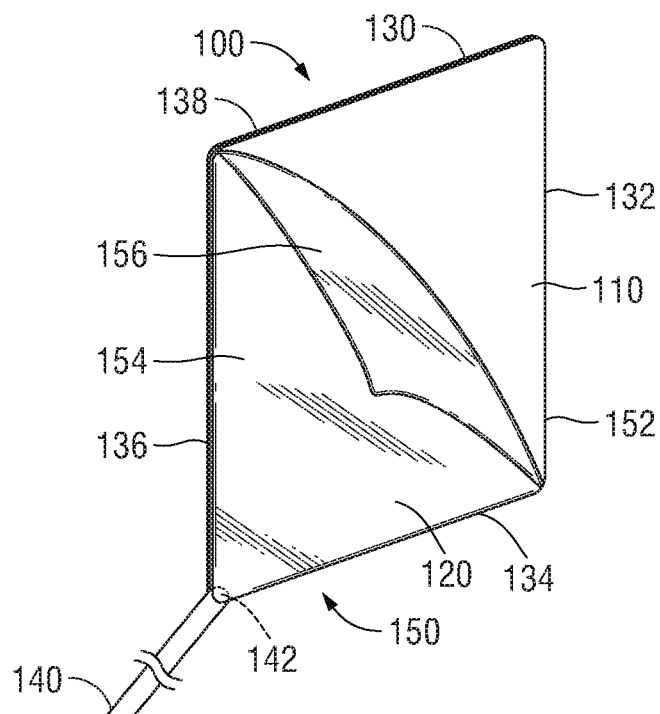
FIG. 3 is a perspective view of the surgical packaging of FIG. 1 in an unfurled configuration.

With additional reference to FIGS. 2 and 3, in preparation for a surgical procedure, surgical packaging 100 is at least partially opened, e.g., from the furled configuration (FIG. 1) to a partially unfurled configuration (FIG. 2) or the unfurled configuration (FIG. 3). More specifically, the cover layer(s) 120 of surgical packaging 100 are separated from the base layer(s) 110 along one or more sides 132-138 of outer perimeter 130 of surgical packaging 100, e.g., via peeling the cover layers(s) 120 from a corner of outer perimeter 130 of surgical packaging 100. With the cover layer(s) 120 at least partially separated from the base layer(s) 110, as illustrated in FIG. 2, the surgical components 200-500 (FIG. 1) are accessible and may thus be removed from surgical packaging 100.

Once the surgical components 200-500 (FIG. 1) are removed from surgical packaging 100, surgical packaging 100, if not already unfurled, may be unfurled to the unfurled configuration (FIG. 3). The unfurled configuration does not require surgical packaging 100 to be completely unfurled to a single layer thickness but, rather, corresponds to a configuration wherein surgical packaging 100 has been sufficiently unfurled for use in a surgical procedure, e.g., as a surgical drape. In embodiments, surgical packaging 100 may include multiple unfurled configurations enabling surgical packaging 100 to define different configurations for use in different manners and/or for different purposes in a surgical procedure.

In embodiments where provided, drape line 140 is separated from the base layer(s) 110 and/or the cover layer(s) 120 along at least a portion of the length of drape line 140 as part of the unfurling of surgical packaging 100. In embodiments, drape line 140 may be connected or connectable to an opening 142 (FIG. 3) defined between the base layer(s) 110 and the cover layer(s) 120 to serve as a drain for fluid collected by surgical packaging 100, as detailed below.

Referring to FIG. 3, in embodiments, in the unfurled configuration or one of the unfurled configurations (in embodiments where multiple unfurled configurations are provided), surgical packaging 100 may define a funnel-shaped configuration 150 including a mouth 152 formed via separation of the base layer(s) 110 from the cover layer(s) 120, or in any other suitable manner, and a body 154 formed via portions of base layer(s) 110 and/or cover layer(s) 120 that remain connected to one another. Funnel-shaped configuration 150 may further define an opening 142 opposite mouth 152. Opening 142, as noted above, is connected or configured to connect to drape line 140 such that any fluid passing through mouth 152 and collected by body 154 may flow through opening 142 to drape line 140 to be directed to a suitable collection assembly, e.g., a collection canister (not shown). In embodiments, funnel-shaped configuration 150 may further include one or more flaps 156 extending outwardly from mouth 152. Flaps 156 may be formed from one or more layers of material and may define any suitable configuration, e.g., rectangular, triangular, etc.

In other embodiments or in another unfurled configuration (in embodiments where multiple unfurled configurations are provided), surgical packaging 100 may be unfurled (or further unfurled) to define a sheet, e.g., a rectangular-shaped sheet, having one or more layers of material and defining an exposed surface area greater (in embodiments, two, three, four, or more times larger) than surgical packaging 100 in the furled configuration thereof. In such embodiments, the sheet of surgical packaging 100 may be utilized as a surgical barrier or divider during a surgical procedure.

Figure 4:
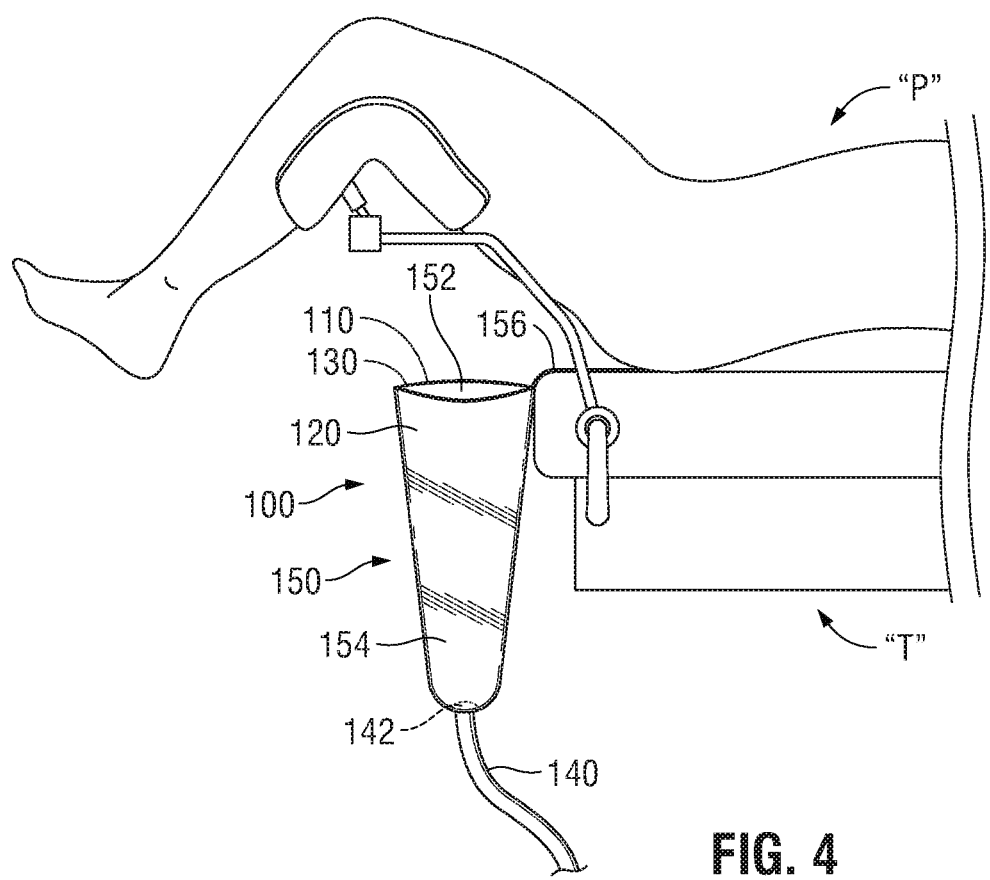
FIG. 4 is a side view illustrating use of the surgical packaging of FIG. 1 in the unfurled configuration positioned under a patient in use during a surgical procedure.

Turning to FIG. 4, surgical packaging 100 is illustrated in the unfurled, funnel-shaped configuration 150 in use during, for example, an intrauterine tissue resection procedure. More specifically, surgical packaging 100 is positioned with one of the flaps 156 thereof positioned underneath a patient "P," e.g., between the patient "P" and the operating table "T," with body 154 of surgical packaging 100 in the funnel-shaped configuration 150 depending from the flap 156 and an end of the operating table "T." Further, drape line 140 is connected to opening 142 defined within body 154. In use, fluids leaked during the intrauterine tissue resection procedure are collected, under gravity, through mouth 152 and body 154 of surgical packaging 100 in the funnel-shaped configuration 150 thereof. These fluids flow, under gravity, from body 154, through opening 142, to drape line 140 which directs the fluid to the collection assembly.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:
1. A device facilitating surgery, comprising:
  surgical packaging including at least one base layer and at least one cover layer, the surgical packaging transitionable from a furled configuration to an unfurled configuration, wherein:
  in the furled configuration, the at least one base layer and the at least one cover layer are connected to one another along at least a portion of a perimeter of the surgical packaging such that the surgical packaging is configured to enclose at least one surgical component therein;
  in the unfurled configuration, at least a portion of the connection between the at least one base layer and the at least one cover layer is broken to at least partially separate the at least one base layer from the at least one cover layer such that the surgical packaging is configured for use as a surgical drape during a surgical procedure; and
  in the unfurled configuration, the at least one base layer and the at least one cover layer define an inner surface of the surgical drape, the inner surface of the surgical drape configured to capture surgical fluids in the surgical drape,
  wherein in the unfurled configuration, the surgical packaging defines a funnel-shaped configuration including a body defining a mouth having a first width defined at one end of the body, and an opening having a second width narrower than the first width defined at an opposite end of the body, the opening configured to drain the surgical fluids captured in the drape from the surgical packaging.

2. The device according to claim 1, wherein the surgical packaging further includes a drape line attached to at least one of the at least one base layer or the at least one cover layer, the drape line connected to or connectable to the opening in the unfurled configuration of the surgical packaging.

3. The device according to claim 1, wherein, in the unfurled configuration, the surgical packaging defines an exposed surface area greater than an exposed surface area of the surgical packaging in the furled configuration.

4. The device according to claim 3, wherein, in the unfurled configuration, the exposed surface area is at least two times greater than the exposed surface area in the furled configuration.

5. A system facilitating surgery, comprising:
at least one surgical component; and
surgical packaging including at least one base layer and at least one cover layer, the surgical packaging transitionable from a furled configuration to an unfurled configuration, wherein:
in the furled configuration, the at least one base layer and the at least one cover layer are connected to one another along at least a portion of a perimeter of the surgical packaging to enclose the at least one surgical component therein; and
in the unfurled configuration, at least a portion of the connection between the at least one base layer and the at least one cover layer is broken to at least partially separate the at least one base layer from the at least one cover layer such that the at least one surgical component may be removed from the surgical packaging and such that the surgical packaging is configured for use as a surgical drape during a surgical procedure; and
in the unfurled configuration, the at least one base layer and the at least one cover layer define an inner surface of the surgical drape, the inner surface of the surgical drape configured to capture surgical fluids in the surgical drape
wherein in the unfurled configuration, the surgical packaging defines a funnel-shaped configuration including a body defining a mouth having a first width defined at one end of the body, and an opening having a second width narrower than the first width defined at an opposite end of the body, the opening configured to drain the surgical fluids captured in the drape from the surgical packaging.

6. The system according to claim 5, wherein the at least one surgical component is configured for use during a tissue resection procedure and wherein the surgical packaging is configured to collect leaked fluid during the tissue resection procedure.

7. The system according to claim 5, wherein the funnel-shaped configuration further defines an opening at an opposite end of the body, and wherein the surgical packaging further includes a drape line attached to at least one of the at least one base layer or the at least one cover layer, the drape line connected to or connectable to the opening in the unfurled configuration of the surgical packaging.

8. The system according to claim 5, wherein, in the unfurled configuration, the surgical packaging defines an exposed surface area greater than an exposed surface area of the surgical packaging in the furled configuration.

9. The system according to claim 8, wherein, in the unfurled configuration, the surgical packaging defines an exposed surface area at least two times greater than the exposed surface area of the surgical packaging in the furled configuration.

10. The system according to claim 5, wherein the at least one surgical component includes a plurality of single-patient-use components.

* * * * *